(12) United States Patent
Miklosovic

(10) Patent No.: US 8,357,164 B2
(45) Date of Patent: Jan. 22, 2013

(54) SURGICAL PUNCH

(75) Inventor: Miroslav Miklosovic, Stuttgart (DE)

(73) Assignee: S.u.A. Martin GmbH & Co. KG (DE)

( * ) Notice: Subject to any disclaimer, the term of this patent is extended or adjusted under 35 U.S.C. 154(b) by 153 days.

(21) Appl. No.: 13/045,740

(22) Filed: Mar. 11, 2011

(65) Prior Publication Data
US 2011/0245834 A1    Oct. 6, 2011

(30) Foreign Application Priority Data
Mar. 30, 2010  (DE) .......................... 10 2010 013 459

(51) Int. Cl.
*A61B 17/3205* (2006.01)
*A61B 17/56* (2006.01)

(52) U.S. Cl. .......................... 606/83; 606/184; 600/567

(58) Field of Classification Search .................... 606/83, 606/84, 114, 170, 174, 184; 30/124, 182, 30/184, 241, 242; 600/567
See application file for complete search history.

(56) References Cited

U.S. PATENT DOCUMENTS

| | | | |
|---|---|---|---|
| 3,902,498 A * | 9/1975 | Niederer ........................ 606/170 |
| 5,026,375 A * | 6/1991 | Linovitz et al. .................. 606/79 |
| 5,484,441 A * | 1/1996 | Koros et al. ...................... 606/79 |
| 5,601,585 A * | 2/1997 | Banik et al. ..................... 606/180 |
| 5,766,177 A | 6/1998 | Lucas-Dean et al. |
| 8,133,237 B2 * | 3/2012 | Oostman et al. ............... 606/133 |
| 2006/0184175 A1* | 8/2006 | Schomer et al. ................ 606/83 |
| 2006/0224084 A1* | 10/2006 | Vetter et al. ..................... 600/567 |
| 2007/0123890 A1* | 5/2007 | Way et al. ........................ 606/79 |
| 2008/0045858 A1* | 2/2008 | Tessitore et al. ............... 600/567 |
| 2008/0300507 A1* | 12/2008 | Figueredo et al. ............. 600/567 |

FOREIGN PATENT DOCUMENTS

| DE | 69834350 | 2/2007 |
|---|---|---|
| DE | 102008034287 | 2/2010 |

* cited by examiner

*Primary Examiner* — Thomas Barrett
*Assistant Examiner* — Michael T Schaper
(74) *Attorney, Agent, or Firm* — Akerman Sentefitt; Peter A. Chiabotti

(57) ABSTRACT

A surgical punch has a cartridge for collecting the resected chips cut off in successive punch cuts. The cartridge is a replaceable disposable commodity. The cartridge consists of a casing and a tooth rail which is guided longitudinally displaceable relative to the casing. Once the cartridge is inserted, the casing is fixed on the upper part of the punch, while the tooth rail is fixed on the lower part of the punch. A transport serration is formed in the casing. The tooth rail has a retaining serration. During the opening and closing movement of the punch, the transport serration and the retaining serration interact as transport mechanism which displaces the cut off resected chips in the cartridge in the proximal direction.

8 Claims, 10 Drawing Sheets

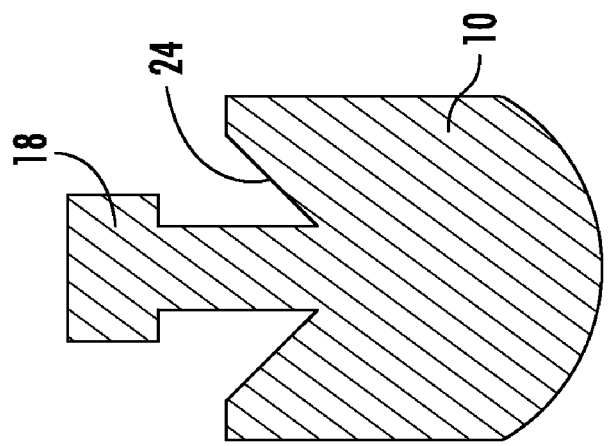
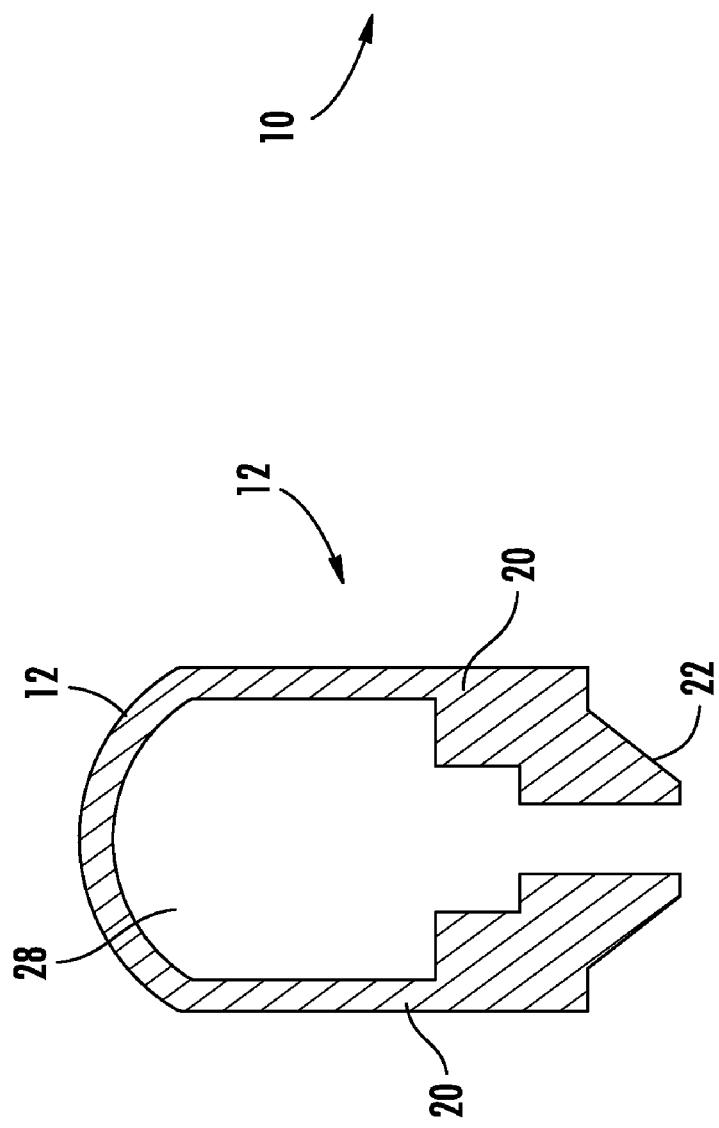

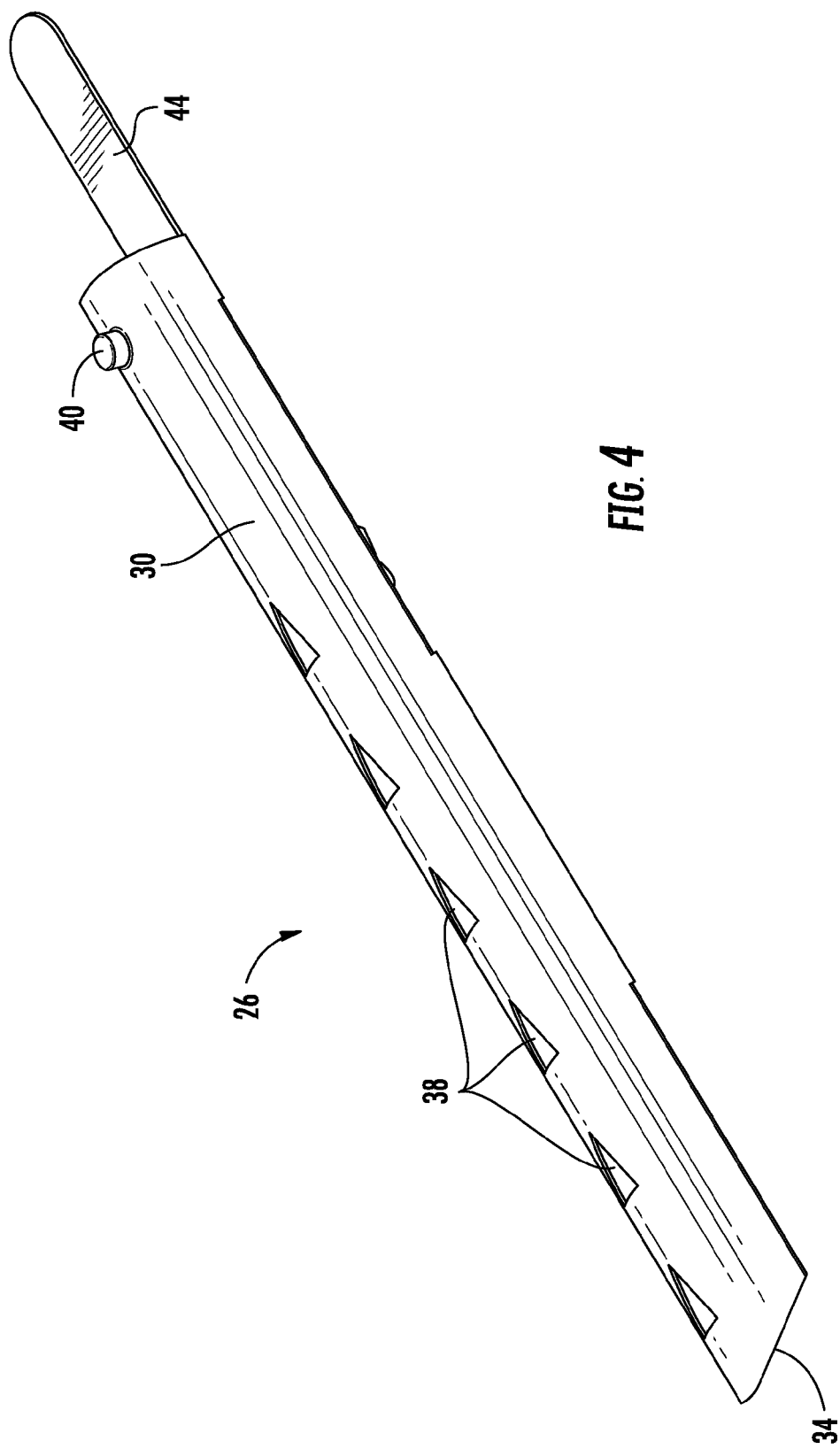

SURGICAL PUNCH

CROSS REFERENCE TO RELATED APPLICATIONS

This application claims the benefit of German Patent Application No. DE 10 2010 013 459.7 filed Mar. 30, 2010, which is hereby incorporated by reference in it's entirety.

DESCRIPTION

The invention relates to a surgical punch.

Surgical punches of this type serve for removing bone, cartilage and other tissue parts. These parts are punched out in the form of small resected tissue chips, the size of which is determined by the size of the punch foot and the punch blade. To resect larger regions, usually, a plurality of punch cuts has to be carried out. In order that it is not required to remove the punch from the surgical wound after each punch cut to remove the resected chip, it is known to collect a relatively high number of cut off resected chips in a collection chamber of the punch.

From U.S. Pat. No. 5,582,618 A, a surgical punch is known with which the successively cut off resected chips are pushed by means of a punch foot into a collection chamber. In order to retain the already collected resected chips during the subsequent closing movement of the punch within the collection chamber, a retaining serration running in the longitudinal direction is provided. The collection chamber is formed by a hollow space in the punch so that emptying the collection chamber is difficult.

From U.S. Pat. No. 7,011,663 B2, a surgical punch is known which has an upper part which is guided longitudinally displaceable and on which a replaceable storage chamber is distally attached. Here, the distal end of the storage chamber forms the punch blade. Since the punch blade must have a high precision and stability, this punch is hardly suitable to produce the storage chamber as inexpensive disposable article.

The invention is based on the object to configure a surgical punch of the aforementioned generic kind with a collection chamber for a high number of resected chips in such a manner that an inexpensive production and a simple handling are possible.

SUMMARY OF THE INVENTION

This object is solved by a surgical punch having the structures and features described herein.

In case of the surgical punch according to the invention, the collection chamber is configured as cartridge which can be replaceably inserted in the distal end of the punch. The cartridge has a sleeve-like casing in which the punched out resected chips are collected. The cartridge is integrated in a tooth rail which is guided displaceable relative to the casing. When inserting the cartridge into the punch, the casing is fixed on the upper part of the punch in an axially non-displaceable manner, while the tooth rail is non-displaceably fixed on the lower part of the punch. In the casing, a transport serration is formed which consists of a row of teeth running in the longitudinal direction. The tooth rail has a retaining serration which also consists of a row of teeth running in the longitudinal direction. The teeth each have a tip pointing in a proximal direction so that the resected chips can be pushed in the proximal direction over the transport serration of the casing as well as over the retaining serration of the tooth rail, but are prevented by the teeth from moving in the distal direction. The transport serration of the casing of the cartridge and the retaining serration of the tooth rail form an active transport mechanism which, when actuating the punch, successively transports each of the cut off resected chips into the cartridge. Once the cartridge is filled or the surgical procedure is finished, the cartridge can be removed in a simple manner from the punch and can be replaced by a new empty cartridge. The cartridge can be produced in a cost-efficient manner from plastic or as punched and bent part from a thin sheet metal so that the cartridge can be produced as inexpensive disposable commodity. Emptying, cleaning and sterilizing the collection chamber is therefore no longer required.

In order to reliably place each of the cut off resected chips into the cartridge, the cartridge is inserted into the upper part of the punch in such a manner that the open distal end of the cartridge lies directly behind the punch blade of the upper part and abuts against the inner contour of the punch blade. Thereby it is achieved that the punch foot of the lower part comes close to the distal end of the cartridge when closing the punch and pushes the cut off resected chip into said cartridge so that the chip can be collected by the transport mechanism of the cartridge. It is advantageous here if the distal edge of the open end of the casing of the cartridge is provided with an inwardly directed tooth rim by which that resected chip is collected which is pushed by the punch foot into the cartridge.

In a particularly advantageous embodiment, the punch blade of the upper part encompasses the punch foot of the lower part so that at the end of the closing movement of the punch, the punch foot plunges into the punch blade. This has the advantage, on the one hand, that the tissue between punch foot and punch blade is cut off by a shearing cut which makes cutting hard and tough bone and cartilage tissue easier. On the other hand, with the punch completely closed, the punch foot can now plunge into the punch blade and can move directly up the distal end of the inserted cartridge so that the cut off resected chip is reliably and completely pushed into the cartridge even if a soft tissue is involved.

BRIEF DESCRIPTION OF DRAWINGS

The invention is explained in more detail hereinafter by means of an exemplary embodiment illustrated in the drawing. In the figures:

FIG. 2 shows a cross-section through the upper part of the punch according to the line A-A in FIG. 1, FIG. 3 shows a cross-section through the lower part of the punch according to the line A-A in FIG. 1, FIG. 4 shows a cartridge for the punch in a perspective view from above.

DETAILED DESCRIPTION

Figure 1:
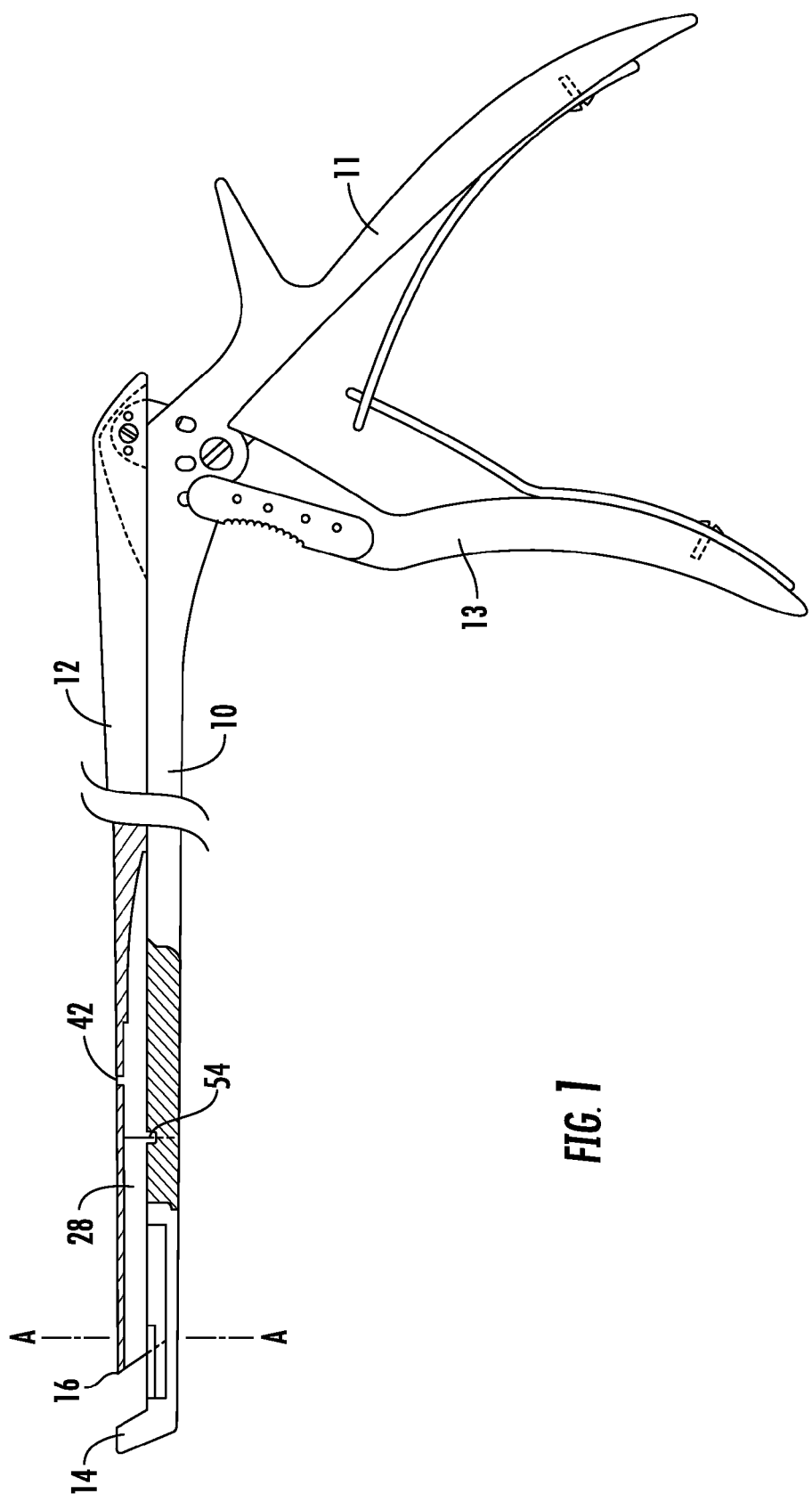
FIG. 1 shows a side view of a punch with a partial cross-section of the distal end.
Figure 5:
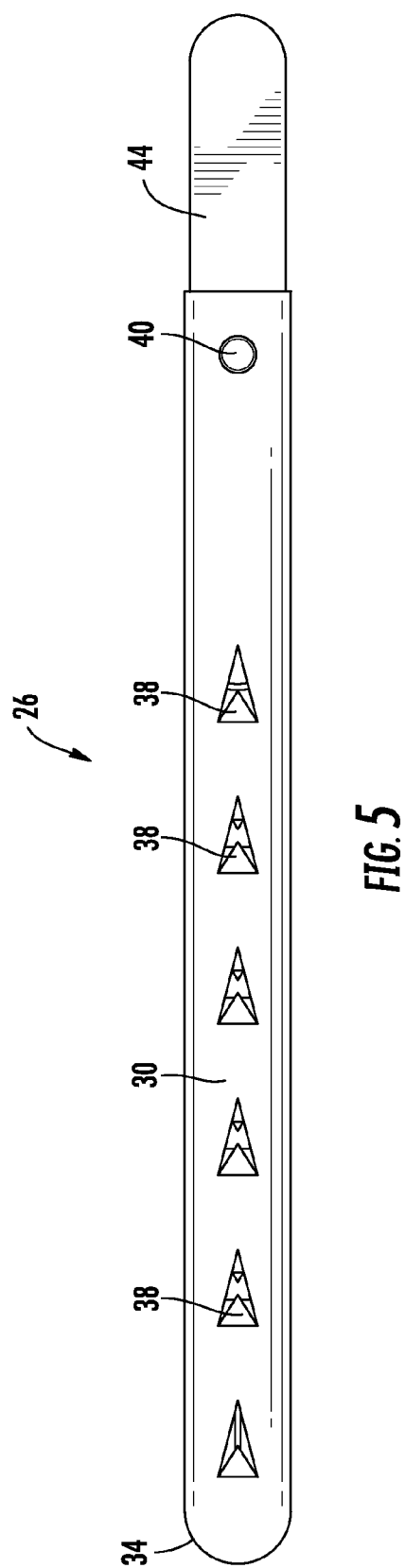
FIG. 5 shows the cartridge in a top view.
Figure 6:
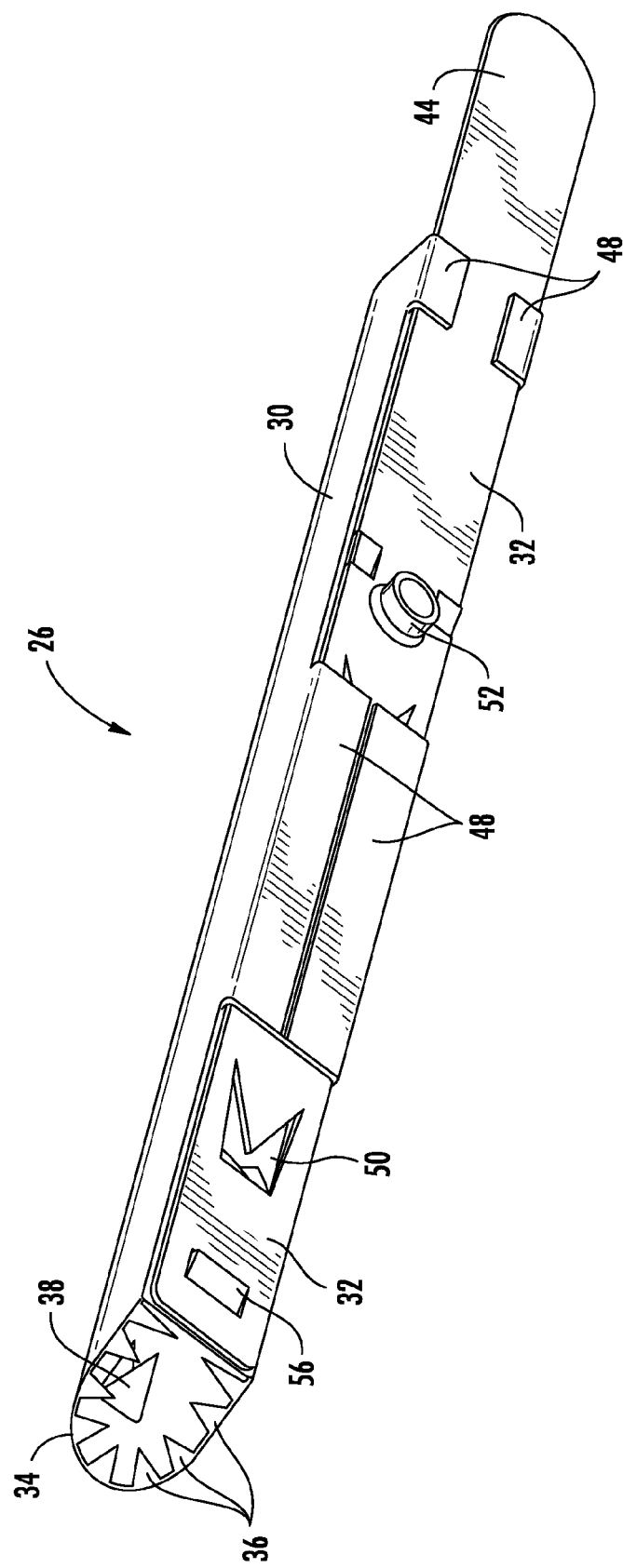
FIG. 6 shows the cartridge in a perspective view from below.
Figure 7:
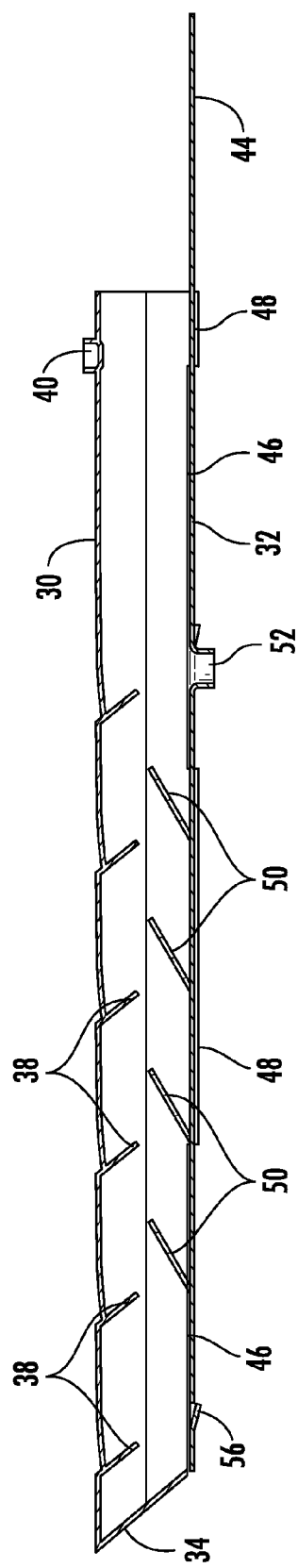
FIG. 7 shows an axial longitudinal section through the cartridge.
Figure 8:
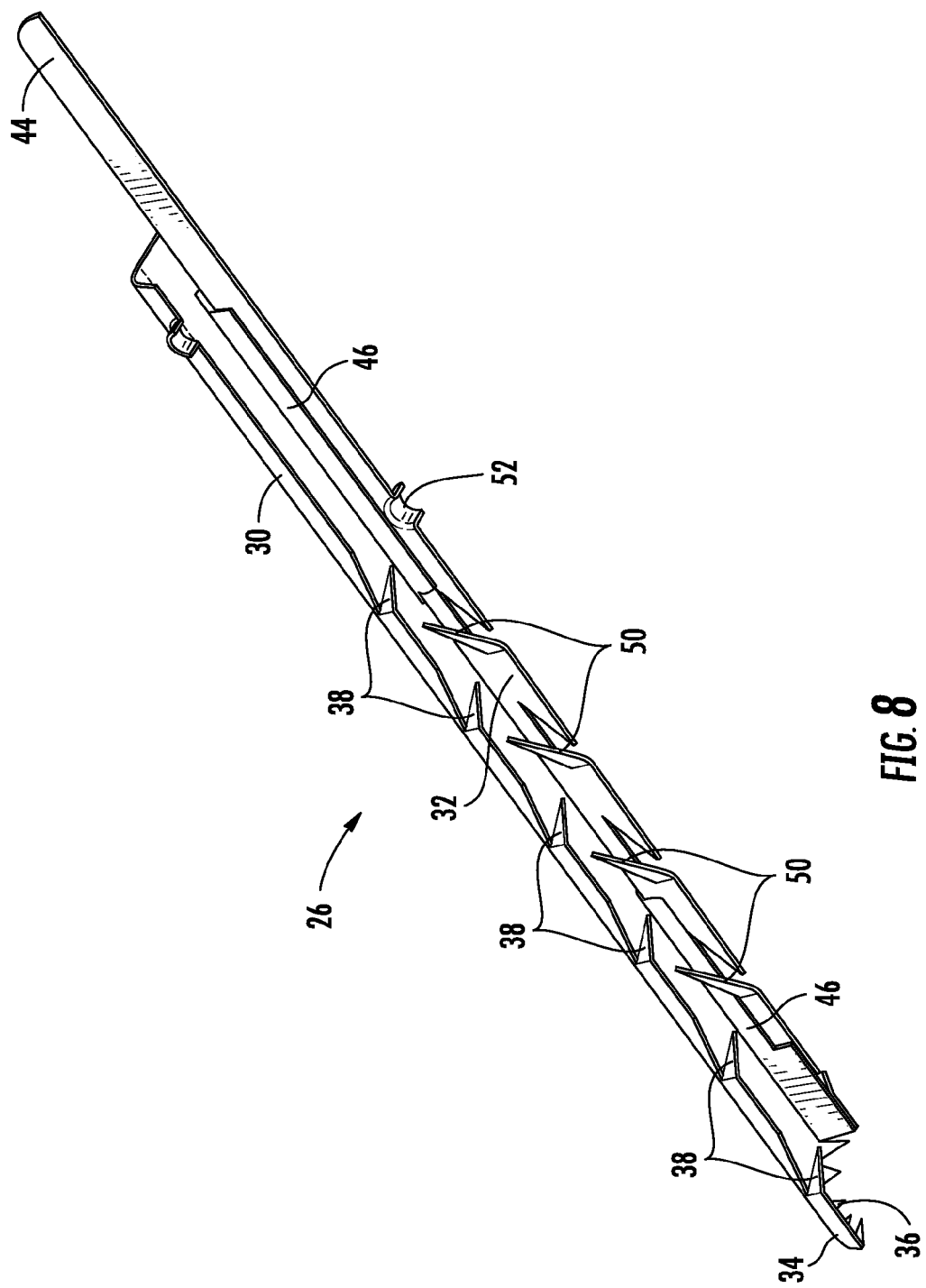
FIG. 8 shows in a perspective view an axial longitudinal section through the cartridge.
Figure 9:
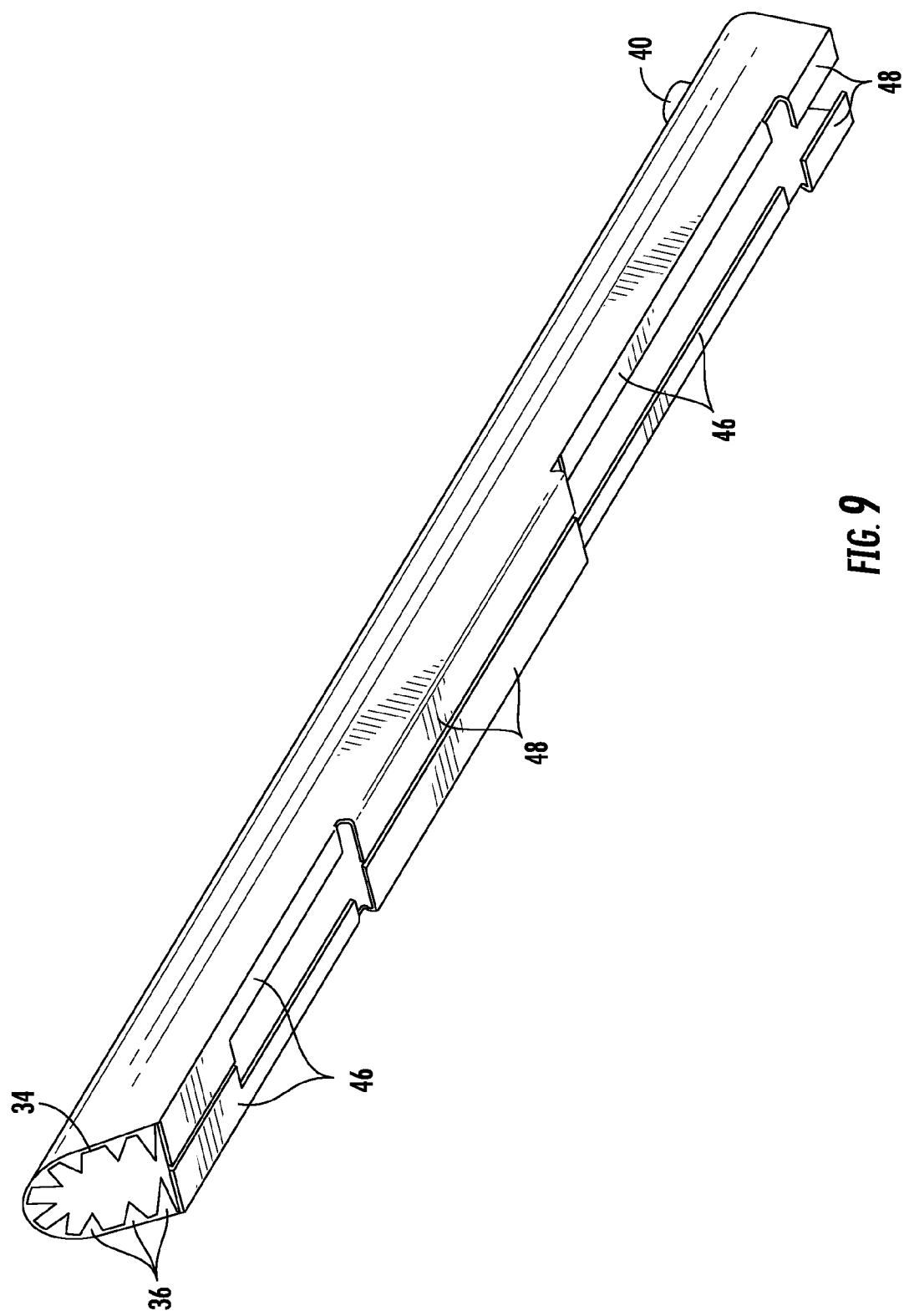
FIG. 9 shows a perspective view of the casing of the cartridge.
Figure 10:
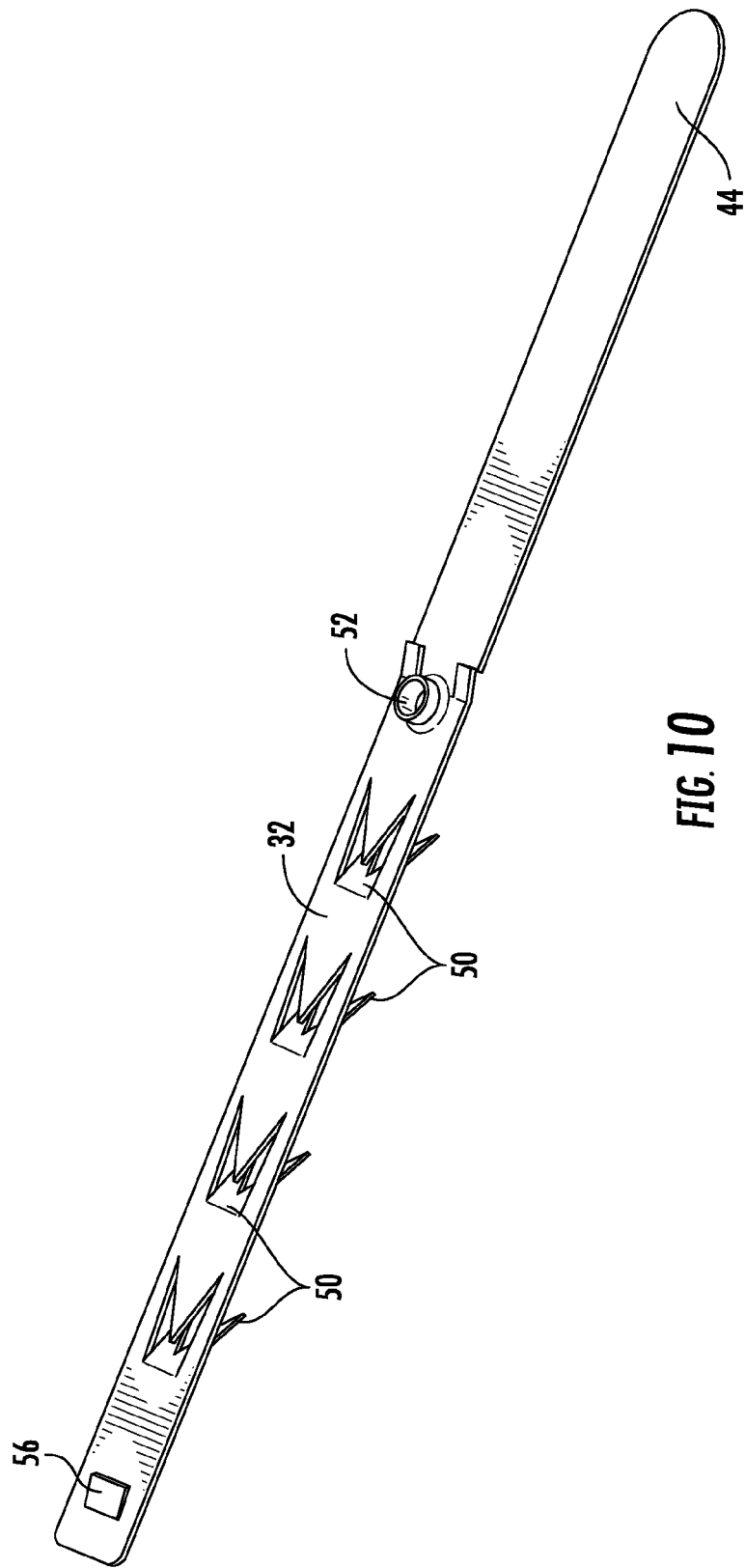
FIG. 10 shows a perspective view of the tooth rail of the cartridge.
Figure 11:
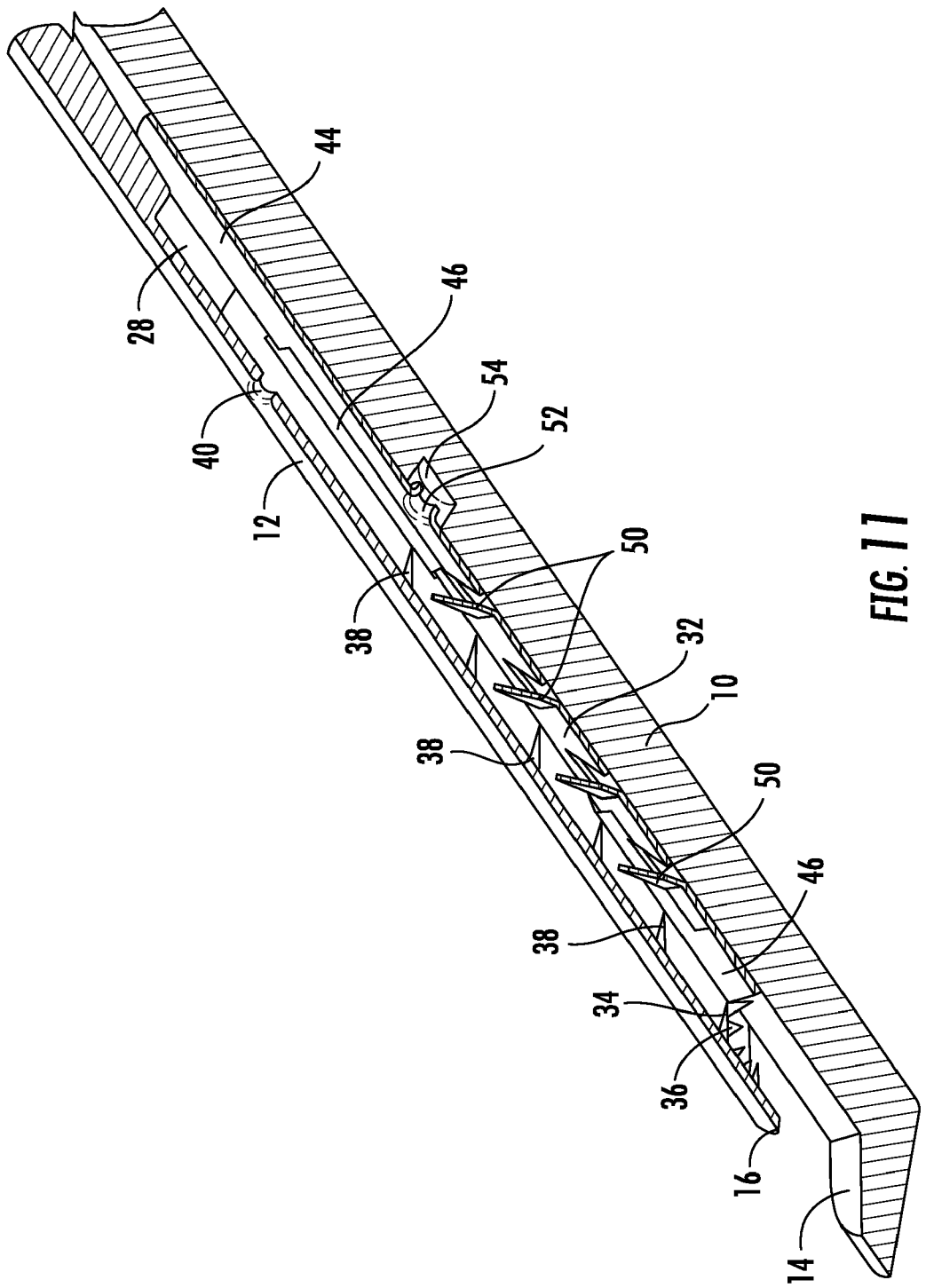
FIG. 11 shows in a perspective view an axial longitudinal section through the distal end of the punch with inserted cartridge.

A surgical punch for resecting bone, cartilage or other tissue has a lower part 10 (shaft) on which an upper part 12

(pusher) is guided in a longitudinally displaceable manner. At the proximal end of the punch, the lower part 10 is connected to a fixed handle part 11. A handle part 13 which is pivotable towards the fixed handle part 11 is engaged with the proximal end of the upper part 12. At the distal end of the lower part 10, an angled punch foot 14 is integrally formed thereon. The distal end of the upper part 12 is formed as punch blade 16, the horseshoe-shaped contour of which corresponds to the outer circumferential contour of the punch foot 14. When pivoting the pivotable handle part 13 towards the fixed handle part 11, the upper part 12 is displaced on the lower part 10 in the distal direction. During this closing movement, the punch blade 16 is slid over the punch foot 14, and the bone, cartilage or other tissue which is present between the punch foot 14 and the punch blade 16 is cut off in the form of a resected chip by means of the shearing cut of punch foot 14 and punch blade 16.

The longitudinal displacement path of the upper part 12 is limited in the proximal direction by a locking mechanism. Once the locking mechanism is unlocked, the upper part 12 can be displaced in the proximal direction into a release position in which the upper part 12 is released from the guide at the lower part 10 and can be lifted off the lower part 10.

In order that the punch blade 16 precisely encompasses the punch foot 14 for the shearing cut, the upper part 12 is guided in the distal end region on the lower part 10 in the following manner. The lower part 10 has a guide web 18 which proximally joins the punch foot 14 and which is directed towards the upper part 12 and which has a T-shaped cross-sectional profile. Said T-shaped guide web 18 is enclosed and engaged from underneath on both sides by guide cheeks 20 which are integrally formed adjacent to the punch blade 16 on the upper part 12. At their lower edge 22, the guide cheeks 20 are inwardly beveled in a wedge-shaped manner and engage with said beveled lower edge 22 with guide grooves 24 upwardly widening in a dovetailed manner which are formed on both sides of the guide web 18 in the lower part 10. Due to the engagement of the beveled lower edges 22 of the guide cheeks 20 with the guide grooves 24, the punch blade 16 is supported against spreading apart in a positive-locking manner. Thereby it is ensured that even in case of high cutting forces which can occur, e.g., when cutting bones or cartilages, the punch blade 16 is not forced outwards which could affect a precise shearing cut.

If a plurality of cutting processes is carried out successively, the resected chips cut off with each cutting process can be collected in the punch without the need to remove the punch from the operating field. A cartridge 26 serves for collecting the successively cut off resected chips. The cartridge 26 has the shape of a longitudinal hollow sleeve and is replaceable and can be inserted in a corresponding longitudinal cavity 28 which is incorporated in the upper part's 12 side facing the lower part 10. The cartridge 26 consists of a casing 30 in which a tooth rail 32 is guided in a longitudinally displaceable manner. The casing 30 can consist of plastic but is preferably made as a punched and bent part from a thin sheet metal, the thickness of which is, for example, approximately 0.2 mm. The casing 30 has a substantially U-shaped cross-section, the shape of which corresponds to the shape of the punch blade 16. Corresponding to the punch blade 16, the distal open end 34 is beveled rearwardly towards the lower part 10 at an angle of, e.g., approximately 130°. If the cartridge 26 is inserted in the cavity 28 of the upper part 12, the distal end 34 of the casing 30 is positioned at a small proximal distance behind the punch blade 16. This distance corresponds to the penetration depth of the punch foot 14 into the punch blade 16 during the closing movement of the upper part 12 during the punch cut. With the punch completely closed, the punch foot 14 thus moves directly up to the open distal end 34 of the casing 30. At the edge of the distal end 34 of the casing 30, a tooth rim 36 is formed. The tooth rim 36 is generated in that during punching the sheet metal for the casing 30, triangular teeth are punched out at the edge of the distal end 34, which teeth are then bent into the interior of the casing 30 so that their tips are directed in the proximal direction towards the inside of cavity of the cartridge 26.

In the upwardly curved upper side of the casing 30, a transport serration 38 is formed. The transport serration 38 is formed by a row of teeth running in the longitudinal direction of the casing 30, which teeth are punched out in a triangular shape during punching the casing 30 and are bent into the interior of the casing 30. The teeth of the transport serration 38 are bent inwardly at an angle of, e.g., approximately 30°, wherein the tips of the triangles point in the proximal direction.

At the proximal end of the casing 30, at its curved upper side, an outwardly directed projection 40 is formed which engages with a recess 42 of the upper part 12 when inserting the cartridge 26 into the cavity 28. Thereby, the casing 30 is secured in the cavity 28 of the upper part 12 against axial displacement and is fixed therein.

The casing's 30 open side facing the lower part 10 is closed by the tooth rail 32. The tooth rail 32 can consist of plastic, but is preferably a punched and bent part which is made from a thin sheet metal with a thickness of, e.g., 0.2 mm. The width of the tooth rail 32 corresponds to the width of the open lower side of the casing 30. In the longitudinal direction, the tooth rail 32 extends over the length of the casing 30 and, with an end plate 44, projects in the proximal direction beyond the casing 30. The tooth rail 32 is guided at the lower side of the casing 30 and is displaceable in the longitudinal direction. For this purpose, support flanges 46 are bent inwardly at a right angle at the lower longitudinal edges of the casing 30, wherein the tooth rail 32 rests on said support flanges. In the longitudinal direction between the support flanges 46, guide flanges 48 are likewise bent inwardly at a right angle, which guide flanges encompass the tooth rail 32 and retain the tooth rail 32 resting on the support flanges 46. Thereby, the tooth rail 32 is guided between the support flanges 46 and the guide flanges 48 in a longitudinally displaceable manner.

A tab 56 downwardly bent at the distal end of the tooth rail 32 abuts against the guide flange 48 when the tooth rail 32 is proximally displaced thereby preventing that the tooth rail 32 can be withdrawn from the casing 30 in the proximal direction. This embodiment is advantageous when the cartridge 26 with the collected resected chips is being disposed of. If the resected chips are to be removed from the cartridge 26, e.g., for diagnostic purposes, the tab 56 is not required. Then, after the cartridge 26 is removed, the tooth rail 32 can be withdrawn from the casing 30 in the axial direction. The retaining serration 50 then carries the resected chips accumulated in the cartridge 26 along so that they can easily be removed.

The tooth rail 32 has a retaining serration 50. The retaining serration 50 is formed by a row of teeth which runs centrally in the longitudinal direction in the tooth rail 32, which teeth are punched out in the form of a double-spike from the sheet metal of the tooth rail 32 and are bent upwardly. The teeth of the retaining serration 50 are bent here at an angle of, e.g., approximately 30°, wherein the tips of the double-spikes point in the proximal direction.

Once the cartridge 26 is inserted into the cavity 28 of the upper part 12, the upper part 12 is placed onto the lower part 10. In doing so, a downwardly directed projection 52 arranged at the proximal end of the tooth rail 32 engages with a recess 54 of the lower part 10, whereby the tooth rail 32 is fixed on the lower part 10 and is non-displaceable in the longitudinal direction.

The end plate 44 of the tooth rail 32 is slightly bent pointing downward. When joining the upper part 12 and the lower part 10 together with the cartridge 26 being inserted, the downwardly bent end plate 44 abuts under elastic deformation against the upper side of the lower part 10. When lifting the upper part 12 off the lower part 10, the end plate 44 lifts off the upper part 12 due to its elastic pretension so that the cartridge 26 can be conveniently grasped at the end plate 44 and can be removed.

During the use of the punch for successive punch cuts, the cut off resected chips are collected in the cartridge 26 in the following manner.

During the longitudinal movement of the upper part 12 relative to the lower part 10, the casing 30 fixed in the upper part 12 moves together with the upper part 12 relative to the lower part 10 and the tooth rail 32 fixed in the lower part 10. During the closing movement for the punch cut, the upper part 12 is displaced in the distal direction until the punch blade 16 encompasses the punch foot 14 so that a resected chip is cut off. In doing so, the punch foot 14 plunges into the punch blade 16 until the punch foot 14 reaches the distal end 34 of the casing 30 of the cartridge 26. Thereby, the punch foot 14 pushes the cut off resected chip into the distal end of the casing 30, where the chip is collected and retained by the tooth rim 36. Thereby it is ensured that not only dimensionally stable bone or cartilage chips get into the cartridge but also resected chips from a soft tissue substance which is not dimensionally stable.

After this, the punch is opened again for the next punch cut. During said proximally directed opening movement, the upper part 12 carries the casing 30 along in the proximal direction. The resected chip introduced into the distal end of the casing 30 is retained by the tooth rim 36 in the casing 30 and thus is also carried along in the proximal direction. In doing so, the resected chip is drawn across the retaining serration 50 of the tooth rail 32 retained in the lower part 10, which is possible due to the form and elasticity of the retaining serration's 50 teeth, which form is directed in the proximal direction.

If the upper part 12 with the casing 30 fixed therein is moved again in the distal direction for the next punch cut, the resected chip is retained during said closing movement by the retaining serration 50 of the tooth rail 32. The casing 30 can slide with its transport serration 38 over the retained resected chip because the teeth of the transport serration 38 are directed in the proximal direction and have an elastic deformability.

In this manner, the resected chip is transported in the casing 30 of the cartridge 26 during the closing movement in the proximal direction and the distal end is free again for receiving the resected chip cut off during the next punch cut. With each following punch cut, the resected chips already collected in the cartridge 26 are retained by the retaining serration 50 of the tooth rail 32 and are transported further in the distally moving casing 30 in the proximal direction. During the subsequent opening movement of the punch, the resected chips are retained by the retaining serration 38 in their respective position in the casing 30. In this manner, the cartridge 26 is gradually filled during the successive punch cuts with the cut off resected chips, wherein said chips are transported in the proximal direction in the cartridge 26 without experiencing any congestion.

Once the cartridge 26 is filled after, for example, approximately 20 to 25 punch cuts, the cartridge 26 can be easily removed after lifting the upper part 12 off the lower part 10 and can be replaced by a new empty cartridge 26. The cartridge 26 is a disposable commodity which can be produced in an inexpensive manner.

REFERENCE NUMBER LIST

10 Lower part
11 Fixed handle part
12 Upper part
13 Pivotable handle part
14 Punch foot
16 Punch blade
18 Guide web
20 Guide cheeks
22 Lower edge
24 Guide grooves
26 Cartridge
28 Cavity
30 Casing
32 Tooth rail
34 Distal end
36 Tooth rim
38 Transport serration
40 Projection of 30
42 Recess
44 End plate
46 Support flanges
48 Guide flanges
50 Retaining serration
52 Projection of 32
54 Recess
56 Tab

What is claimed:

1. A surgical punch, comprising:
a lower part;
an upper part which is guided on the lower part in a longitudinally displaceable manner and which can be lifted off said lower part;
a punch foot arranged at a distal end of the lower part;
a punch blade arranged at a distal end of the upper part and which interacts with the punch foot during a distally directed closing movement of the upper part;
a collection chamber arranged in the upper part, in which resected chips cut off by the punch blade are transported, the collection chamber having a retaining serration running in a longitudinal direction of the collection chamber, the retaining serration retaining the resected chips in the collection chamber during the closing movement of the upper part;
a cartridge, wherein the cartridge is configured to be inserted into a distal end of the punch, the cartridge having a casing which forms the collection chamber and which is fixed in a non-displaceable manner in the upper part once the cartridge is inserted,
wherein the retaining serration is formed on a tooth rail which is guided in the cartridge in a longitudinally displaceable manner and which is fixed in the lower part in a non-displaceable manner once the cartridge is inserted,
wherein a distal end of the casing is open and abuts against an inner contour of the punch blade once the cartridge is inserted,
wherein a transport serration is formed in the casing, the transport serration running in a longitudinal direction and which, during a proximally directed opening movement of the upper part, pushes the resected chips collected in the casing over the retaining serration of the tooth rail.

2. The punch according to claim 1, wherein an inner tooth rim is formed at the open distal end of the casing.

3. The punch according to claim 1, wherein the punch blade encompasses the punch foot during the closing movement.

4. The punch according to claim 3, wherein the punch foot plunges into the punch blade up to the distal end of the casing when the punch is closed.

5. The punch according to claim 1, wherein the casing and the tooth rail are punched and bent parts made from a sheet metal and that the retaining serration and the transport serration are each punched out and bent out from said sheet metal.

6. The punch according to claim 1, wherein the casing has an outer projection which engages with a recess of the upper part for non-displaceably fixing the casing, and that the tooth rail has an outer projection which engages for a non-displaceably fixing with a recess of the lower part.

7. The punch according to claim 1, wherein the tooth rail projects with an end plate in the proximal direction beyond the casing of the cartridge, and that the end plate is elastically pre-tensioned so that it lifts off the upper part once the upper part is lifted off the lower part.

8. The punch according to claim 1, wherein the cartridge is replaceable.

\* \* \* \* \*